United States Patent
Acharya et al.

(10) Patent No.: US 6,922,462 B2
(45) Date of Patent: Jul. 26, 2005

(54) METHOD, SYSTEM AND COMPUTER PRODUCT FOR PLAQUE CHARACTERIZATION

(75) Inventors: Kishore Acharya, Brookfield, WI (US); Priya Gopinath, Waukesha, WI (US); Jianying Li, New Berlin, WI (US); Darin Okerlund, Muskego, WI (US); Matthew Joseph Walker, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 62 days.

(21) Appl. No.: 10/064,621

(22) Filed: Jul. 31, 2002

(65) Prior Publication Data

US 2004/0022359 A1 Feb. 5, 2004

(51) Int. Cl.[7] .............................................. H05G 1/64
(52) U.S. Cl. ................ 378/98.11; 378/98.9; 378/98.12
(58) Field of Search ........................ 378/5, 8, 53, 54, 378/95, 98.9, 98.11, 98.12; 600/431

(56) References Cited

U.S. PATENT DOCUMENTS

| | | | | |
|---|---|---|---|---|
| 4,029,963 A | * | 6/1977 | Alvarez et al. ................. 378/5 |
| 4,559,557 A | * | 12/1985 | Keyes et al. ............. 378/98.11 |
| 4,611,341 A | * | 9/1986 | Brody ...................... 378/98.11 |
| 4,662,379 A | * | 5/1987 | Macovski ................... 600/428 |
| 4,686,695 A | * | 8/1987 | Macovski ................... 378/146 |
| 4,736,398 A | * | 4/1988 | Graeff et al. ............. 378/98.3 |
| 4,945,478 A | * | 7/1990 | Merickel et al. ............ 382/131 |
| 5,123,037 A | * | 6/1992 | Picard et al. .............. 378/98.2 |
| 5,247,559 A | * | 9/1993 | Ohtsuchi et al. ............... 378/53 |
| 5,396,530 A | * | 3/1995 | Tsutsui et al. ........... 378/98.11 |
| 5,459,769 A | * | 10/1995 | Brown ........................... 378/4 |
| 5,485,492 A | * | 1/1996 | Pelc .............................. 378/5 |
| 5,661,774 A | * | 8/1997 | Gordon et al. ................ 378/101 |
| 5,908,387 A | | 6/1999 | LeFree et al. .............. 600/425 |
| 6,233,304 B1 | | 5/2001 | Hu et al. ........................ 378/8 |
| 6,256,368 B1 | | 7/2001 | Hsieh et al. .................... 378/8 |
| 6,278,760 B1 | * | 8/2001 | Ogawa et al. ................. 378/5 |
| 6,298,110 B1 | | 10/2001 | Ning .............................. 378/4 |
| 6,307,910 B1 | | 10/2001 | Acharya et al. ............... 378/4 |
| 6,324,254 B1 | * | 11/2001 | Pflaum ........................ 378/95 |
| 6,337,992 B1 | * | 1/2002 | Gelman .................... 600/425 |
| 6,356,617 B1 | * | 3/2002 | Besch et al. ............. 378/98.11 |
| 6,438,200 B1 | * | 8/2002 | Kita ............................. 378/44 |
| 6,463,121 B1 | * | 10/2002 | Milnes ........................ 378/62 |
| 6,501,827 B1 | * | 12/2002 | Takasawa ................... 378/116 |

* cited by examiner

*Primary Examiner*—Edward J. Glick
*Assistant Examiner*—Allen C. Ho
(74) *Attorney, Agent, or Firm*—Cantor Colburn LLP

(57) ABSTRACT

A method for plaque characterization. The method comprises obtaining a first set of image data created in response to a first x-ray energy level and including a plurality of pixel elements. Each of the first pixel elements corresponds to a unique location in an object being scanned. The method further comprises obtaining a second set of image data created in response to a second x-ray energy level and including a plurality of second pixel elements. Each of the second pixel elements corresponds to one of the first pixel elements and the second x-ray energy level is higher than the first x-ray energy level. The method also comprises calculating a third set of image data in response to the first set of image data and the second set of image data. The calculating includes subtracting each second pixel element from the corresponding first pixel element.

28 Claims, 4 Drawing Sheets

METHOD, SYSTEM AND COMPUTER PRODUCT FOR PLAQUE CHARACTERIZATION

BACKGROUND OF INVENTION

The present disclosure relates generally to a method for plaque characterization and in particular, to a method for using multiple x-ray energy level absortiometry techniques for plaque characterization in cardiac applications.

In at least one known computed tomography (CT) imaging system configuration, an x-ray source projects a fan-shaped beam which is collimated to lie within an X-Y plane of a Cartesian coordinate system, wherein the X-Y plane is generally referred to as an "imaging plane". An array of radiation detectors, wherein each radiation detector includes a detector element, is within the CT system so as to receive this fan-shaped beam. An object, such as a patient, is disposed within the imaging plane so as to be subjected to the x-ray beam wherein the x-ray beam passes through the object. As the x-ray beam passes through the object being imaged, the x-ray beam becomes attenuated before impinging upon the array of radiation detectors. The intensity of the attenuated beam of radiation received at the detector array is responsive to the attenuation of the x-ray beam by the object, wherein each detector element produces a separate electrical signal responsive to the beam attenuation at the detector element location. These electrical signals are referred to as x-ray attenuation measurements.

In addition, the x-ray source and the detector array may be rotated, with a gantry within the imaging plane, around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and the detector array. In an axial scan, the projection data is processed so as to construct an image that corresponds to a two-dimensional slice taken through the object.

One method for reconstructing an image from a set of projection data is referred to as the "filtered back-projection technique". This process converts the attenuation measurements from a scan into discrete integers, ranging from −1024 to +3071, called "Hounsfield Units" (HU) or CT HUs. These CT HU's are used to control the brightness of a corresponding pixel on a cathode ray tube or a computer screen display in a manner responsive to the attenuation measurements. For example, an attenuation measurement for air may convert into an integer value of −1000 HU's (corresponding to a dark pixel) and an attenuation measurement for very dense bone matter may convert into an integer value of +1000 HUs (corresponding to a bright pixel), whereas an attenuation measurement for water may convert into an integer value of 0 HU's (corresponding to a gray pixel). This integer conversion of attenuation value to various shades of gray allows a physician or a technician to determine the density of matter based on the intensity of the computer display.

A strong and graded association exists between coronary calcification and cardiovascular disease. Coronary calcification scores have been used to measure atherosclerotic plaque burden and the extent of angiographically detected coronary artery disease and as a screening tool to predict the extent of cardiovascular disease and to develop risk factor for future cardiac event such as heart attack. Larger, high-density calcified plaques are associated with stable coronary events. Certain plaques are more vulnerable to detaching off the walls of the artery and prompting a blood clot, which travels to the heart and can cause a sudden unanticipated fatal heart attack. This so-called vulnerable plaque is soft because of its high lipid, or fat, content. Soft plaques, also referred to as non-calcified plaques, are not highly calcified and hence calcium scores in such subjects may be minimal indicating that the subject is normal. The effectiveness of a screening tool lies in the early detection of disease and current calcium screening tests may not be effective because they do not account for the measurement of soft plaques.

SUMMARY OF INVENTION

One aspect of the invention is a method for plaque characterization. The method comprises obtaining a first set of image data created in response to a first x-ray energy level and including a plurality of first pixel elements. Each of the first pixel elements corresponds to a unique location in an object being scanned. The method further comprises obtaining a second set of image data created in response to a second x-ray energy level and including a plurality of second pixel elements. Each of the second pixel elements corresponds to one of the first pixel elements and the second x-ray energy level is higher than the first x-ray energy level. The method also comprises calculating a third set of image data in response to the first set of image data and the second set of image data. The calculating includes subtracting each second pixel element from the corresponding first pixel element.

Another aspect of the invention is a method for plaque characterization. The method comprises obtaining a set of image data created in response to an x-ray energy level and an object injected with a contrast agent. The method also comprises locating a vessel of interest in the object and tracking a flow of the contrast agent through the vessel. The soft plaque is identified in the vessel in response to the image data and to the flow. The method also comprises plotting the distribution of the soft plaque and determining the vulnerability of the soft plaque in response to the distribution.

Another aspect of the invention is a system for plaque characterization. The system comprises an imaging system and an object disposed so as to be communicated with the imaging system, wherein the imaging system generates image data responsive to the object. The imaging system generates a first set of image data and a second set of image data responsive to the object. The first set of image data is created in response to a first x-ray energy level and includes a plurality of first pixel elements. Each first pixel element corresponds to a unique location in the object. The second set of image data is created in response to a second x-ray energy level and includes a plurality of second pixel elements. The second x-ray energy level is higher than the first x-ray energy level. The system also comprises a processing device in communication with the imaging system including software to implement a method comprising obtaining the first set of image data, the second set of image data and calculating a third set of image data. The third set of image data is calculated in response to the first set of image data and the second set of image data and includes subtracting each second pixel element from the corresponding first pixel element.

A further aspect of the invention is a computer program product for plaque characterization. The computer program product includes a storage medium readable by a processing circuit and storing instructions for execution by the processing circuit for obtaining a first set of image data created in response to a first x-ray energy level and including a plurality of first pixel elements. Each of the first pixel elements corresponds to a unique location in an object being scanned. The computer program product further includes instructions for obtaining a second set of image data created in response to a second x-ray energy level and including a plurality of second pixel elements. Each of the second pixel elements corresponds to one of the first pixel elements and the second x-ray energy level is higher than the first x-ray energy level. The computer program product further includes instructions for calculating a third set of image data in response to the first set of image data and the second set of image data. The calculating includes subtracting each second pixel element from the corresponding first pixel element.

A further aspect of the invention is a computer program product for plaque characterization. The computer program product includes a storage medium readable by a processing circuit and storing instructions for execution by the processing circuit including instructions for obtaining a set of image data created in response to an x-ray energy level and an object injected with a contrast agent. The method also comprises locating a vessel of interest in the object and tracking a flow of the contrast agent through the vessel. The soft plaque is identified in the vessel in response to the image data and to the flow. The method also comprises plotting the distribution of the soft plaque and determining the vulnerability of the soft plaque in response to the distribution.

Further aspects of the invention are disclosed herein. The above discussed and other features and advantages of the present invention will be appreciated and understood by those skilled in the art from the following detailed description and drawings.

BRIEF DESCRIPTION OF DRAWINGS

Referring to the exemplary drawings wherein like elements are numbered alike in the several FIGURES.

DETAILED DESCRIPTION

In an embodiment of the present invention, multiple energy and single energy absortiometry imaging is utilized to detect soft plaques and the progression of cardiovascular disease. In accordance with an exemplary embodiment of the present invention, while a method, system and computer product for plaque characterization is described hereinbelow with reference to a computed tomography (CT) system, it should be understood that the method, system and computer product of the present invention may be applied to other imaging systems, such as magnetic resonance imaging (MRI).

Figure 1:
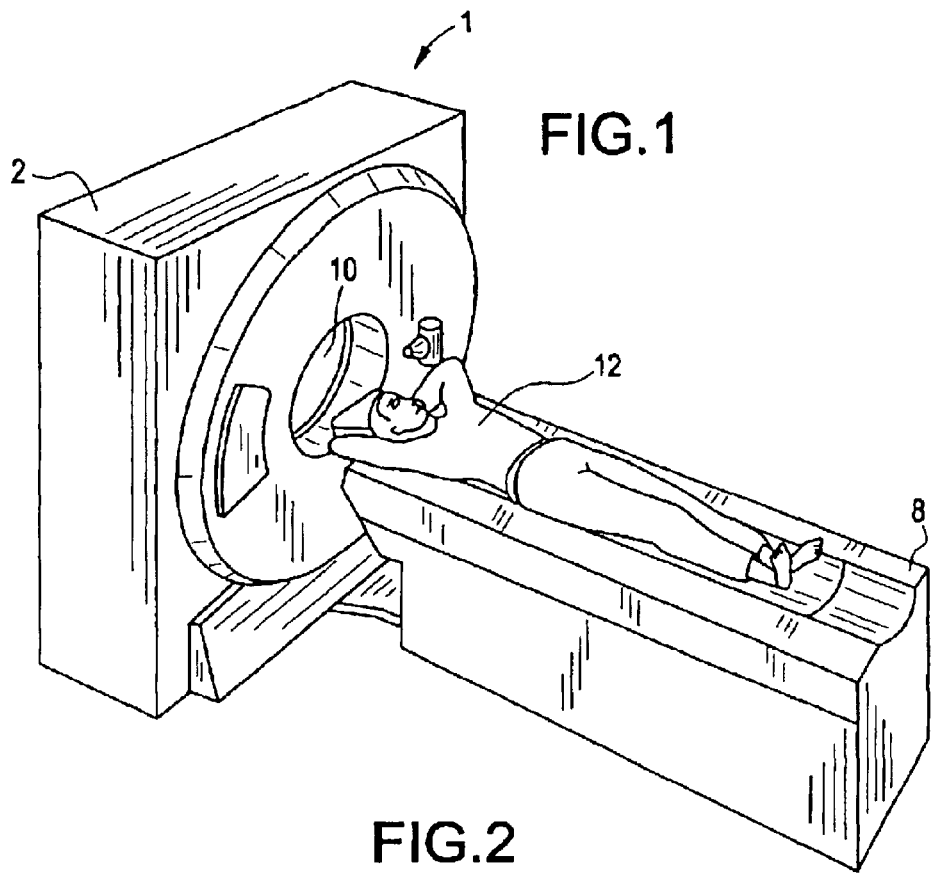
FIG. 1 is a perspective view of a CT imaging system and a patient disposed for imaging in accordance with an exemplary embodiment of the present invention.
Figure 2:
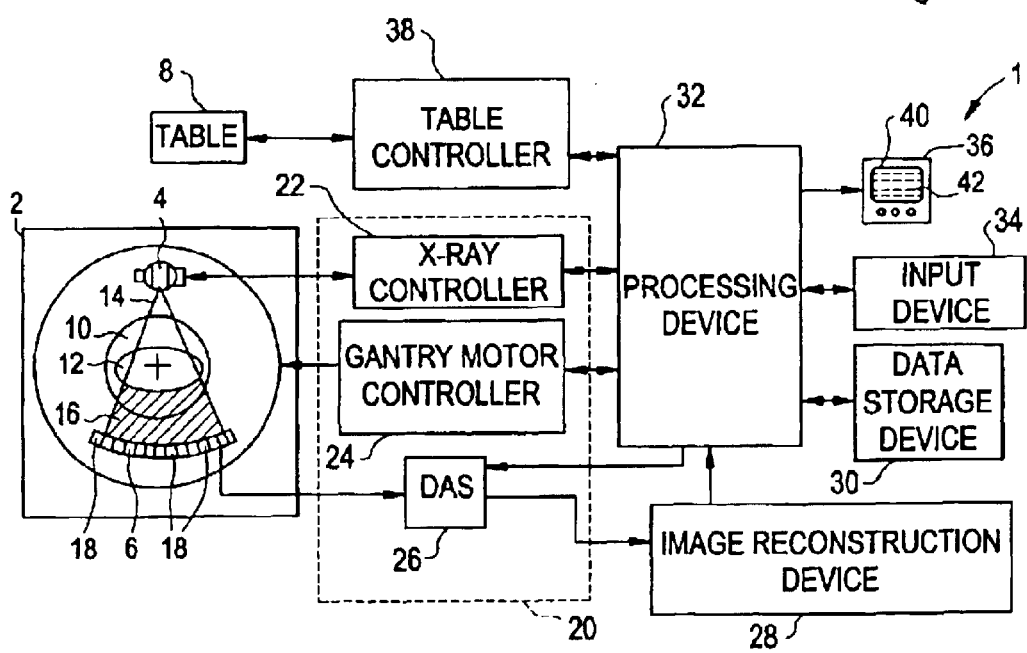
FIG. 2 is a block schematic diagram of a CT imaging system in accordance with an exemplary embodiment of the present invention.

Referring to FIG. 1 and FIG. 2, a representative CT imaging system 1 is shown, including a gantry 2 having an x-ray source 4, a radiation detector array 6, a patient support structure 8 and a patient cavity 10, wherein the x-ray source 4 and the radiation detector array 6 are opposingly disposed so as to be separated by the patient cavity 10. In an exemplary embodiment, a patient 12 is disposed upon the patient support structure 8, which is then disposed within the patient cavity 10. The x-ray source 4 projects an x-ray beam 14 toward the radiation detector array 6 so as to pass through the patient 12. In an exemplary embodiment, the x-ray beam 14 is collimated by a collimate (not shown) so as to lie within an X-Y plane of a Cartesian coordinate system referred to as an "imaging plane". After passing through and becoming attenuated by the patient 12, the attenuated x-ray beam 16 is received by the radiation detector array 6. In an exemplary embodiment, the radiation detector array 6 includes a plurality of detector elements 18 wherein each of said detector elements 18 receives an attenuated x-ray beam 16 and produces an electrical signal responsive to the intensity of the attenuated x-ray beam 16.

In addition, in an exemplary embodiment, the x-ray source 4 and the radiation detector array 6 are rotatingly disposed relative to the gantry 2 and the patient support structure 8, so as to allow the x-ray source 4 and the radiation detector array 6 to rotate around the patient support structure 8 when the patient support structure 8 is disposed within the patient cavity 10. X-ray projection data is obtained by rotating the x-ray source 4 and the radiation detector array 6 around the patient 12 during a scan. In an exemplary embodiment, the x-ray source 4 and the radiation detector array 6 communicate with a control mechanism 20 associated with the CT imaging system 1. In an exemplary embodiment, the control mechanism 20 controls the rotation and operation of the x-ray source 4 and the radiation detector array 6.

In an exemplary embodiment, the control mechanism 20 includes an x-ray controller 22 communicating with a x-ray source 4, a gantry motor controller 24, and a data acquisition system (DAS) 26 communicating with a radiation detector array 6. The x-ray controller 22 provides power and timing signals to the x-ray source 4, the gantry motor controller 24 controls the rotational speed and angular position of the x-ray source 4, and the radiation detector array 6 and the DAS 26 receive the electrical signal data produced by detector elements 18 and convert this data into digital signals for subsequent processing. In an exemplary embodiment, the CT imaging system 1 also includes an image reconstruction device 28, a data storage device 30 and a processing device 32, wherein the processing device 32 communicates with the image reconstruction device 28, the gantry motor controller 24, the x-ray controller 22, the data storage device 30, an input device 34 and an output device 36. The CT imaging system 1 can also include a table controller 38 in communication with the processing device 32 and the patient support structure 8, so as to control the position of the patient support structure 8 relative to the patient cavity 10.

In accordance with an exemplary embodiment, the patient 12 is disposed on the patient support structure 8, which is then positioned by an operator via the processing device 32 so as to be disposed within the patient cavity 10. The gantry motor controller 24 is operated via processing device 32 so as to cause the x-ray source 4 and the radiation detector array 6 to rotate relative to the patient 12. The x-ray controller 22 is operated via the processing device 32 so as to cause the x-ray source 4 to emit and project a collimated x-ray beam 14 toward the radiation detector array 6 and hence toward the patient 12. The x-ray beam 14 passes through the patient 12 so as to create an attenuated x-ray beam 16, which is received by the radiation detector array 6.

The detector elements 18 receive the attenuated x-ray beam 16, produce electrical signal data responsive to the intensity of the attenuated x-ray beam 16 and communicate this electrical signal data to the DAS 26. The DAS 26 then converts this electrical signal data to digital signals and communicates both the digital signals and the electrical signal data to the image reconstruction device 28, which performs high-speed image reconstruction. This information is then communicated to the processing device 32, which stores the image in the data storage device 30 and displays the digital signal as an image via output device 36. In accordance with an exemplary embodiment, the output device 36 includes a display screen 40 having a plurality of discrete pixel elements 42.

An exemplary embodiment of the present invention utilizes multiple x-ray images over the organ of interest in an interleaving fashion while performing CT scanning. Lower x-ray energy levels are known to be effective in imaging soft tissue (e.g., lipids) while higher x-ray energy levels are known to be effective in imaging high-density structures (e.g., calcified plaques). An exemplary embodiment includes one thousand views in half a second gantry rotation, resulting in two views per millisecond being produced. Using the exemplary waveform 300 depicted in FIG. 3, and assuming that the frequency of the kilovolt modulation waveform is also one thousand hertz, one view at the 140 kilovolt (kV) x-ray energy level and another at the 80 kV x-ray energy level would be produced every millisecond. For the generation of images at each kV setting, it would be desirable to have at least two hundred and forty degrees of data. At the end of the scan period, five hundred views of the 140 kV data and five hundred views of the 80 kV data would be produced. In an exemplary embodiment, in order to obtain the misregistration effects from a two successive scan approach. In addition, using the interleaving approach can result in dose savings compared to performing two separate scans.

Figure 3:
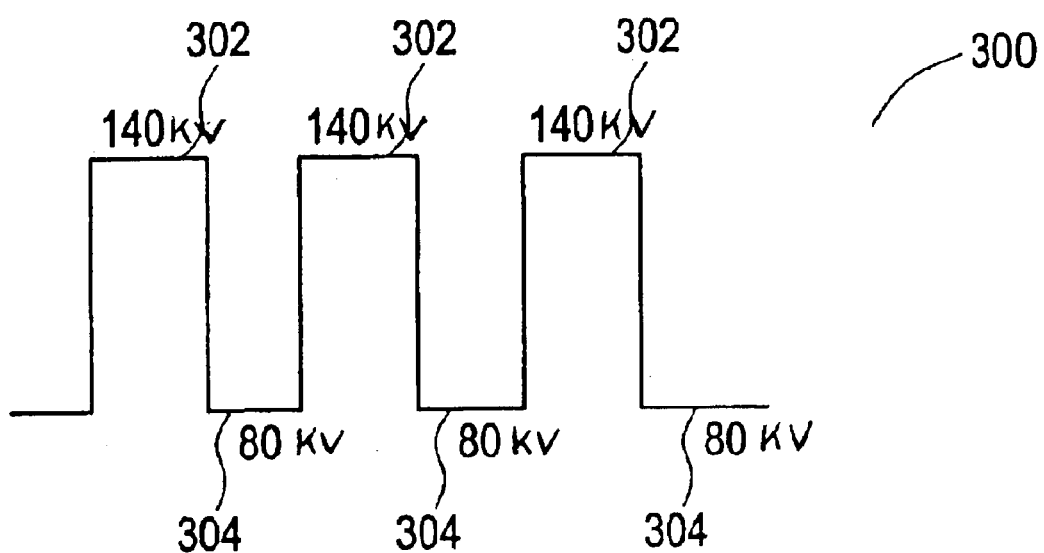
FIG. 3 depicts the use of multiple x-ray energies in an interleaving pattern as utilized in an exemplary embodiment of the present invention.

In an alternate exemplary embodiment, the kV modulations may not be as fast as a one millisecond time period. Therefore, a couple of views at one kV may be taken before switching to the next kV. In this alternate exemplary embodiment, the difference between the views may need to be interpolated using advanced interpolation of views. In another alternate exemplary embodiment of the present invention, the switching may not occur precisely as depicted in FIG. 3. In this case the calibration modules would need to account for the range of kV settings between the higher x-ray energy level and lower x-ray energy level during the switching. In addition the detector should be able to handle different x-ray energy levels.

Figure 4:
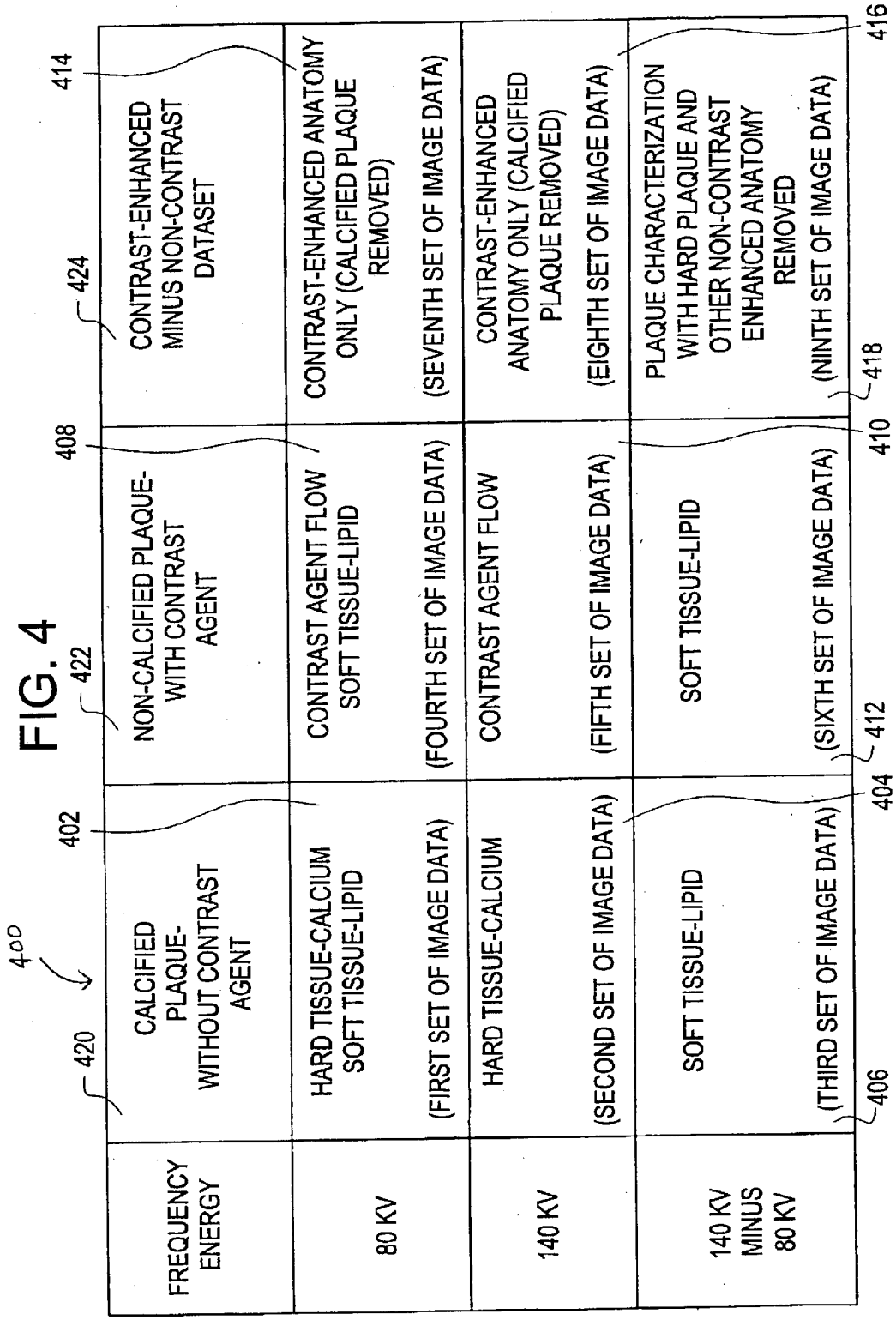
FIG. 4 is a matrix including high x-ray energy level and low x-ray energy level x-ray images with and without a contrast agent.

An embodiment of the present invention includes using the interleaving technique depicted in FIG. 3 for both contrast and non-contrast images. This would result in a matrix of image data with two different kV settings and with both contrast and non-contrast images such as the one depicted in FIG. 4. In addition, as depicted in FIG. 4, image subtraction could be used to generate a difference image set for each x-ray energy level to provide information on the nature of the soft plaques. In an exemplary embodiment, the data in the column labeled 420 can be used for viewing calcified plaque and the soft lipids within the calcified plaque. Using the lower x-ray energy level, 80 kV, and no contrast agent produces a first set of image data 402 that includes the hard tissue and the soft tissue (e.g., lipid or fat) portions of the calcified plaque. Using the higher x-ray energy level, 140 kV, and no contrast agent produces a second set of image data 404 that includes the hard tissue (e.g., calcium deposits) portion of the calcified plaque. Subtracting the second set of image data 404 from the first set of image data 402 results in a third set of image data 406 that includes the soft tissue portion of the calcified plaque. In this manner, the soft tissue portion of calcium plaque can be viewed and analyzed.

In an exemplary embodiment, the data in the column labeled 422 can be used for viewing non-calcified plaque. Using the lower x-ray energy level, 80 kV, and a contrast agent produces a fourth set of image data 408 that includes the contrast agent flow and the soft tissue (e.g., lipid or fat) portion of the non-calcified plague. Using the higher x-ray energy level, 140 kV, and a contrast agent produces a fifth set of image data 410 that includes the contrast agent flow. Subtracting the fifth set of image data 410 from the fourth set of image data 408 results in a sixth set of image data 412 that includes the soft tissue portion of the non-calcified plaque. In this manner, the soft tissue portion of non-calcified plaque can be viewed and analyzed.

In an exemplary embodiment, a composite image can be created by subtracting the non-contrast dataset from the contrast-enhanced dataset as shown in column 424 of FIG. 4. The resulting image can be used for viewing contrast enhanced anatomy. Subtracting the first set of image data 402 from the fourth set of image data 408 results in a seventh set of image data 414 that includes contrast enhanced anatomy only (calcified plaque removed). Subtracting the second set of image data 404 from the fifth set of image data 410 results in an eighth set of image data 416 that includes contrast enhanced anatomy only (calcified plaque removed). Subtracting the third set of image data 406 from the sixth set of image data 412 results in a ninth set of image data 418 that includes plaque characterization with the hard plaque and other non-contrast enhanced anatomy removed. Additional composite images obtained from both set of views (e.g., with the contrast agent and without the contrast agent) can be used to understand plaque characteristics. In an exemplary embodiment, the difference images 406, 412, 418 could be viewed on the display screen 40 once the scanning is complete. The processing device 32 can include instructions for creating and displaying the data in the matrix 400.

Figure 5:
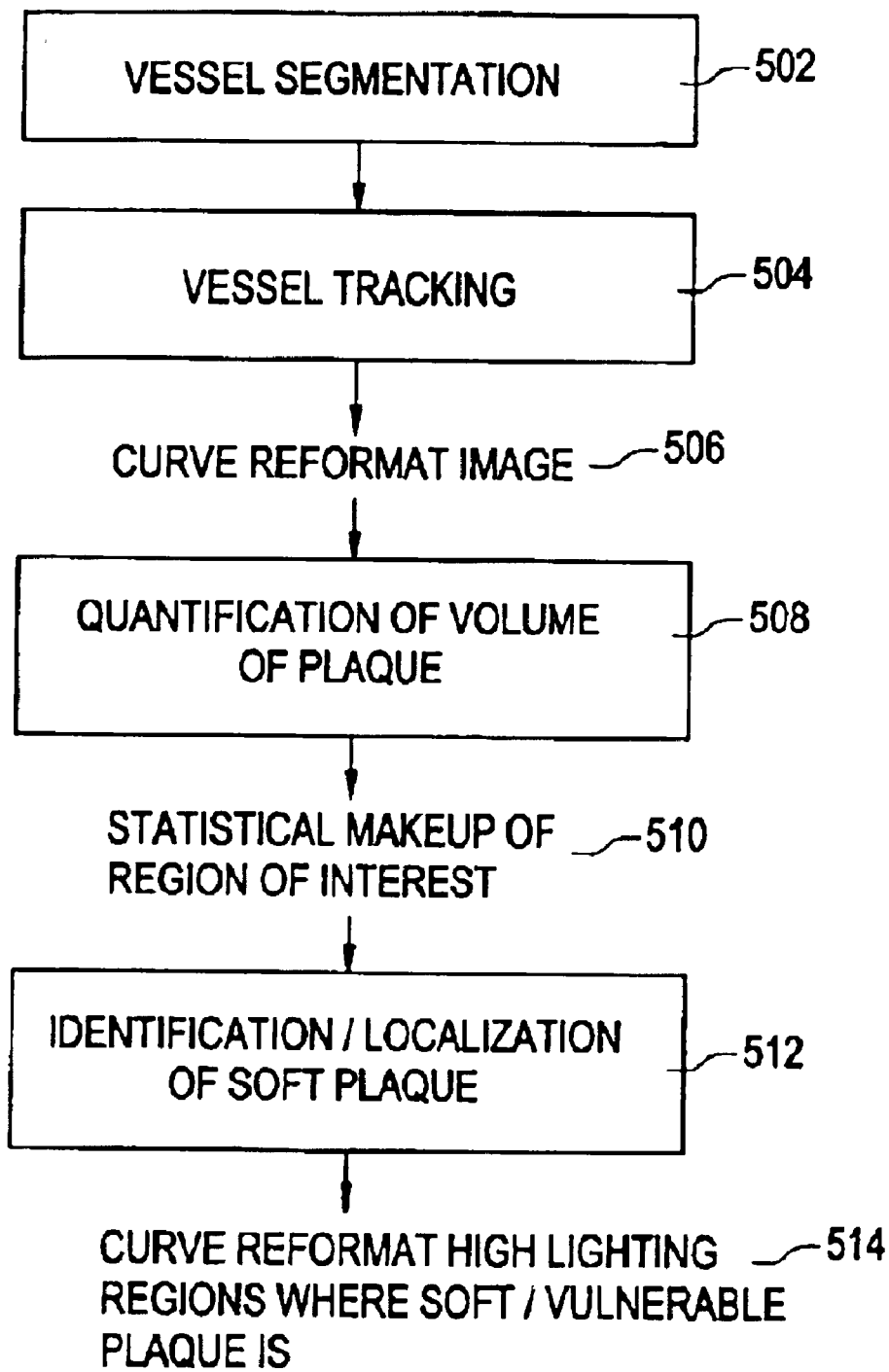
FIG. 5 is a block diagram of an exemplary method for post processing image data using an embodiment of the present invention.

FIG. 5 is a block diagram of an exemplary method for post processing image data using an embodiment of the present invention. The process depicted in FIG. 5 can be used to localize and quantify soft tissue or non-calcified plaque using a contrast image. At step 502, vessel segmentation is performed. Vessel segmentation includes determining the location of the vessel of interest. Next, at step 504, vessel tracking is performed including following the flow of a contrast agent from the beginning of the vessel and plotting the diameter of the vessel to determine where the flow narrows and widens. Vessel tracking can be performed using a high x-ray energy level and a contrast agent as shown in box 410 of FIG. 4. An output from step 504 includes a curve reformat image 506. Next, at step 508, the volume of plaque is quantified by looking at the soft plaque absorption coefficient or if HUs. An input to step 508 includes the curve reformat image 506. Quantifying the plaque and determining plaque characterizations can be performed using the difference between the lower x-ray energy level 304 and the higher x-ray energy level 302 as depicted in box 412 of FIG. 4. In this manner the structure of the plaque can be analyzed. Output from step 508 includes data describing the statistical make-up of the region of interest 510 (e.g., histogram plot of the HU numbers and contour plot). The data describing the statistical make-up of the region of interest 510 is input to step 512. Step 512 performs an identification, or localization, of the soft plaque. Output from this step includes a curve reformat image highlighting regions where the soft, or vulnerable, plaque is located 514. In an exemplary embodiment, the highlights are in color over the original curve reformat image 506.

In an alternate embodiment, single energy abortiometry imaging is utilized to detect soft plaques and the progression of cardiovascular disease. The patient is injected with radio opaque dye, or contrast agent. The image generated by the single x-ray energy level includes calcified plaques, if present, and lumen inside the coronary arteries. Lumen is a long white tracer depicting blood mixed with the contrast agent. The calcified plaques can be detected directly and the non-calcified plaques can be detected indirectly by the narrowing of the lumen. Once the soft plaque is identified, the vulnerability of the plaque can be obtained by the distribution of the CT HU number within the soft plaque from the x-ray energy level scan.

An embodiment of the present invention can be utilized to produce images of the soft tissue portions of both calcified plaque and non-calcified plaque. This can result in a better understanding of the progression of cardiovascular disease. Vulnerable plaques, a variety of non-calcified plaques, have been identified to be the cause of about seventy percent of heart attacks. The ability to produce images that detail the structure of soft tissue plaque, in addition to calcified plaque, can lead to preventing sudden unexplained heart attacks and to the early detection of cardiovascular disease. Firing the x-rays of varying x-ray energy level in an interleaving fashion can reduce the misregistration effects from a two successive scan approach. In addition, using the interleaving approach can result in dose savings compared to performing two separate scans.

Although the preceding embodiments are discussed with respect to medical imaging, it is understood that the image acquisition and processing methodology described herein is not limited to medical applications, but may be utilized in non-medical applications. In addition, the preceding embodiments are discussed with respect to cardiac applications, it is understood that the image acquisition and processing methodology described herein is not limited to cardiac applications, but may be utilized in non-cardiac applications.

As described above, the embodiments of the invention may be embodied in the form of computer-implemented processes and apparatuses for practicing those processes. Embodiments of the invention may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. An embodiment of the present invention can also be embodied in the form of computer program code, for example, whether stored in a storage medium, loaded into and/or executed by a computer, or transmitted over some transmission medium, such as electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method for plaque characterization, the method comprising:

obtaining a first set of image data created in response to a first x-ray energy level and including a plurality of first pixel elements, wherein each said first pixel element corresponds to a unique location in an object being scanned and said first set of image data includes hard tissue and soft tissue calcified plaque data;

obtaining a second set of image data created in response to a second x-ray energy level and including a plurality of second pixel elements, wherein each said second pixel element corresponds to one said first pixel element and wherein said second x-ray energy level is higher than said first x-ray energy level and said second set of image data contains said hard tissue calcified plaque data; and calculating a third set of image data in response to said first set of image data and said second set of image data, wherein said calculating includes subtracting each said second pixel element from said corresponding first pixel element and said third set of image data contains said soft tissue calcified plaque data.

2. The method of claim 1 wherein each said second pixel element is created in close time proximity to each said corresponding first pixel element.

3. The method of claim 2 wherein said close time proximity is one millisecond or less.

4. The method of claim 1 wherein each said second pixel element and each said corresponding first pixel element are created within the same scan in an interleaving pattern.

5. The method of claim 1 wherein said object is a patient.

6. The method of claim 1 wherein said first x-ray energy level is 80 kilovolts.

7. The method of claim 1 wherein said second x-ray energy level is 140 kilovolts.

8. The method of claim 1 wherein said object being scanned was injected with a contrast agent, said first set of image data includes contrast agent flow and soft tissue non-calcified plague data, said second set of image data contains said contrast agent flow non-calcified plague data and said third set of image data contains said soft tissue non-calcified plague data.

9. The method of claim 1 further comprising displaying said first set of image data, said second set of image data and said third set of image data.

10. The method of claim 1 wherein said first set of image data, said second set of image data and said third set of image data were created as non-contrast images, and wherein claim 1 further comprises:

obtaining a fourth set of image data created in response to said first x-ray energy level and including a plurality of fourth pixel elements, wherein each said fourth pixel element corresponds to a said first pixel element, wherein said fourth set of image data was created as a contrast image and said fourth set of image data includes contrast agent flow and soft tissue non-calcified plague data;

obtaining a fifth set of image data created in response to said second x-ray energy level and including a plurality of fifth pixel elements, wherein each said fifth pixel element corresponds to a said fourth pixel element, said fifth set of image data was created as a contrast image and said fifth set of image data contains said contrast agent flow non-calcified plaque data; and calculating a sixth set of image data in response to said fourth set of image data and said fifth set of image data, wherein said calculating a sixth set of image data includes subtracting each said fifth pixel element from said corresponding fourth pixel element and said sixth set of image data contains said soft tissue non-calcified plaque data.

11. The method of claim 10 further comprising displaying said fourth set of image data, said fifth set of image data and said sixth set of image data.

12. The method of claim 10 further comprising:

calculating a seventh set of image data in response to said first set of image data and said fourth set of image data, wherein said calculating a seventh set of image data includes subtracting each said first pixel element from said corresponding fourth pixel element;

calculating an eighth set of image data in response to said second set of image data and said fifth set of image data, wherein said calculating a seventh set of image data includes subtracting each said second pixel element from a corresponding fifth pixel element; and calculating a ninth set of image data in response to said third set of image data and said sixth set of image data, wherein said calculating a ninth set of image data includes subtracting each said third pixel element from a corresponding sixth pixel element.

13. The method of claim 12 further comprising displaying said seventh set of image data, said eighth set of image data and said ninth set of image data.

14. The method of claim 10 further comprising:

calculating a composite set of image data in response to at least one of said first set of image data, said second set of image data, said third set of image data, said fourth set of image data, said fifth set of image data and said sixth set of image data.

15. The method of claim 14 further comprising displaying said composite set of image data.

16. The method of claim 1 further comprising:

locating a vessel of interest in said object, wherein said object was injected with a contrast agent;

tracking a flow of said contrast agent through said vessel; and quantifying plaque in said vessel in response to said third set of image data and to said flow.

17. The method of claim 16 wherein said tracking is performed in response to said second set of image data.

18. The method of claim 16 further comprising determining the characteristics of said plaque in response to said third set of image data.

19. A method for plaque characterization, the method comprising:

obtaining image data created in response to first and second x-ray energy levels and an object injected with a contrast agent;

locating a vessel of interest in said object;

tracking a flow of said contrast agent through said vessel;

identifying soft plaque in said vessel in response to said image data and to said flow;

plotting the distribution of said soft plaque; and determining the vulnerability of said soft plaque in response to said distribution.

20. A system for plaque characterization, the system comprising:

an imaging system generating a first set of image data and a second set of image data responsive to an object, the generating of the first set of image data in response to a first x-ray energy level and generating of the second set of image data in response to a second x-ray energy level, said first set of image data includes a plurality of first pixel elements, each said first pixel element corresponds to a unique location in said object, said first set of image data includes hard tissue and soft tissue calcified plaque said second set of image data includes a plurality of second pixel elements, each said second pixel element corresponds to one said first pixel element, said second x-ray energy level is higher than said first x-ray energy level and said second set of image data contains said hard tissue calcified plague; and a processing device in communication with said imaging system obtaining said first set of image data and said second set of image data from said imaging system and calculating a third set of image data by subtracting each said second pixel element from said corresponding first pixel element wherein said third set of image data contains said soft tissue calcified plaque data.

21. The system of claim 20 wherein said object is a patient.

22. The system of claim 20 wherein said imaging system is a computed tomography imaging system.

23. The system of claim 20 wherein said imaging system is remotely located from said processing device.

24. The system of claim 20 wherein said processing device is in communication with said imaging system over a network.

25. The system of claim 24 wherein said network is the Internet.

26. A computer program product for plaque characterization in cardiac applications, the product comprising:

a storage medium readable by a processing circuit and storing instructions for executing a method for plaque characterization by the processing circuit, the method comprising:

obtaining a first set of image data created in response to a first x-ray energy level and including a plurality of first pixel elements, wherein each said first pixel element corresponds to a unique location in an object being scanned and said first set of image data includes hard tissue and soft tissue calcified plague data;

obtaining a second set of image data created in response to a second x-ray energy level and including a plurality of second pixel elements, wherein each said second pixel element corresponds to one said first pixel element, second x-ray energy level is higher than said first x-ray energy level and said second set of image data contains said hard tissue calcified plaque data; and calculating a third set of image data in response to said first set of image data and said second set of image data, wherein said calculating includes subtracting each said second pixel element from said corresponding first pixel element and said third set of image data contains said soft tissue calcified plague data.

27. The computer program product of claim 26 wherein each said pixel element and said corresponding first pixel element are created with the same scan in an interleaving pattern.

28. A computer program product for plaque characterization in cardiac applications, the product comprising:

a storage medium readable by a processing circuit and storing instructions for executing a method for plague characterization by the processing circuit, the method comprising:

obtaining image data created in response to first and second x-ray energy levels and an object injected with a contrast agent;

locating a vessel of interest in said object;

tracking a flow of said contrast agent through said vessel;

identifying soft plaque in said vessel in response to said image data and to said flow;

plotting the distribution of said soft plaque; and determining the vulnerability of said soft plaque in response to said distribution.

* * * * *

UNITED STATES PATENT AND TRADEMARK OFFICE
CERTIFICATE OF CORRECTION

PATENT NO. : 6,922,462 B2
DATED : July 26, 2005
INVENTOR(S) : Acharya et al.

It is certified that error appears in the above-identified patent and that said Letters Patent is hereby corrected as shown below:

Column 5,
Line 61, after "in order to obtain" delete "the misregistration effects from a two successive scan approach. In addition, using the interleaving approach can result in dose savings compared to performing two separate scans." and insert -- one hundred and eighty plus fan angle degrees worth of data for each set of kV data, one and a third rotations of data for the given specifications would be produced. The exemplary embodiment depicted in FIG. 3 specifies 140 kV as the value of the higher x-ray energy level 302 and 80 kV as the value of the lower x-ray energy level 304. Alternate embodiments of the present invention can utilize a variety of values for both higher x-ray energy level 302 and lower x-ray energy level 304 to produce the results described herein (e.g., 130 kV and 100 kV). --.

Column 7,
Line 26, after "or" delete "if".

Column 9,
Lines 31, 32, 34 and 50, after "non-calcified" delete "plague" and insert -- plaque --; and
Line 46, before "said" delete "wherein".

Column 11,
Lines 7 and 40, after "calcified" delete "plague" and insert -- plaque --.

Column 12,
Line 5, after "element," insert -- said --; and
Line 15, after "calcified" delete "plague" and insert -- plaque --.

Signed and Sealed this

Third Day of January, 2006

JON W. DUDAS
*Director of the United States Patent and Trademark Office*